US009149809B2

(12) United States Patent
Guo et al.

(10) Patent No.: US 9,149,809 B2
(45) Date of Patent: Oct. 6, 2015

(54) THERMAL CYCLER WITH VAPOR CHAMBER FOR RAPID TEMPERATURE CHANGES

(75) Inventors: Kun Guo, Pinole, CA (US); Daniel Y. Chu, Hercules, CA (US); Paul Patt, Lafayette, CA (US); Amir Sadri, Toronto (CA); Roger Tong, Berkeley, CA (US)

(73) Assignee: BIO-RAD LABORATORIES, INC., Hercules, CA (US)

(*) Notice: Subject to any disclaimer, the term of this patent is extended or adjusted under 35 U.S.C. 154(b) by 197 days.

(21) Appl. No.: 13/460,983

(22) Filed: May 1, 2012

(65) Prior Publication Data

US 2013/0143272 A1 Jun. 6, 2013

Related U.S. Application Data

(60) Provisional application No. 61/483,439, filed on May 6, 2011.

(51) Int. Cl.
*C12P 19/34* (2006.01)
*B01L 7/00* (2006.01)

(52) U.S. Cl.
CPC ........... *B01L 7/52* (2013.01); *B01L 2300/0829* (2013.01); *B01L 2300/1822* (2013.01); *B01L 2300/1827* (2013.01); *B01L 2300/1855* (2013.01)

(58) Field of Classification Search
CPC .... B01L 7/52; B01L 2300/0829; C12Q 1/686
See application file for complete search history.

(56) References Cited

U.S. PATENT DOCUMENTS

| | | | | |
|---|---|---|---|---|
| 2,350,348 | A | 6/1944 | Gaugler | |
| 5,924,482 | A * | 7/1999 | Edwards et al. | 165/104.33 |
| 7,727,479 | B2 | 6/2010 | Heimberg et al. | |
| 7,771,933 | B2 | 8/2010 | Arciniegas et al. | |

(Continued)

FOREIGN PATENT DOCUMENTS

| | | | |
|---|---|---|---|
| EP | 1170017 | A1 | 10/2006 |
| EP | 2060324 | A1 | 5/2009 |

(Continued)

OTHER PUBLICATIONS

Extended European Search Report dated Nov. 25, 2014 for EP Application No. 12782793.9, 5 pages.

(Continued)

*Primary Examiner* — Betty Forman
(74) *Attorney, Agent, or Firm* — Kilpatrick Townsend & Stockton LLP

(57) ABSTRACT

Rapid and uniform temperature changes in the wells of a microplate or any thin-walled plate that contains an array of reaction wells or sample receptacles are achieved by the use of heating and cooling elements with a vapor chamber interposed between such elements and the microplate. The upper surface of the vapor chamber and the underside of the sample plate in certain embodiments are complementary in shape, i.e., they have identical but oppositely directed contours in the areas around each of the sample receptacles, to provide continuous surface contact along the surface of each receptacle. In other embodiments, an intermediary plate is placed between the vapor chamber and the well plate, with the top surface of the intermediary plate being complementary in shape to the underside of the well plate.

19 Claims, 6 Drawing Sheets

(56) References Cited

U.S. PATENT DOCUMENTS

| | | | | |
|---|---|---|---|---|
| 2005/0009070 | A1* | 1/2005 | Arciniegas et al. | 435/6 |
| 2006/0246573 | A1* | 11/2006 | Kurane et al. | 435/287.2 |
| 2007/0251670 | A1 | 11/2007 | Peng et al. | |
| 2009/0120104 | A1 | 5/2009 | Federer | |
| 2009/0203082 | A1* | 8/2009 | Schlaubitz et al. | 435/91.2 |
| 2009/0275113 | A1 | 11/2009 | Maltezos et al. | |
| 2010/0203595 | A1* | 8/2010 | Ward et al. | 435/91.2 |
| 2010/0303690 | A1* | 12/2010 | Howell et al. | 422/600 |
| 2011/0023970 | A1 | 2/2011 | Rapp et al. | |

FOREIGN PATENT DOCUMENTS

| | | | |
|---|---|---|---|
| WO | 2004/105947 | A2 | 12/2004 |
| WO | WO2009/030908 | * | 3/2009 |
| WO | 2009/102924 | A1 | 8/2009 |

OTHER PUBLICATIONS

International Search Report and Written Opinion for PCT/US2012/036006, mailed Jul. 6, 2012, 16 pages.

* cited by examiner

THERMAL CYCLER WITH VAPOR CHAMBER FOR RAPID TEMPERATURE CHANGES

CROSS-REFERENCE TO RELATED APPLICATION

This application claims the benefit of U.S. Provisional Patent Application No. 61/483,439, filed May 6, 2011, the contents of which are incorporated herein by reference in their entirety.

BACKGROUND OF THE INVENTION

1. Field of the Invention

This invention relates to sequential chemical reactions of which the polymerase chain reaction (PCR) is one example. In particular, this invention addresses methods and apparatus for performing chemical reactions simultaneously in a multitude of reaction mixtures and independently controlling the reaction in each mixture.

2. Description of the Prior Art

PCR is one of many examples of chemical processes that require a high level of temperature control of reaction mixtures with rapid temperature changes between different stages of the procedure. PCR itself is a process for amplifying DNA, i.e., producing multiple copies of a DNA sequence from a single strand bearing the sequence. PCR is typically performed in instruments that provide reagent transfer, temperature control, and optical detection of the product in a multitude of reaction vessels such as wells, tubes, or capillaries. The process includes a sequence of stages that are temperature-sensitive, different stages being performed at different temperatures and the temperature sequence being repeated in successive cycles.

While PCR can be performed in any reaction vessel, multi-well reaction plates and microfluidics devices with multiple channels are the reaction vessels of choice so that many strands of DNA can be replicated simultaneously. In many applications, PCR is performed in "real-time" and the reaction mixtures are repeatedly analyzed throughout the process, by the detection of light from fluorescently-tagged species in the reaction medium. In other applications, DNA is withdrawn from the medium for separate amplification and analysis. In multiple-sample PCR processes, a preferred arrangement is one in which each sample occupies one well of a multi-well plate or one channel of a multi-channel microfluidics device, and all samples in the plate or the microfluidics device are simultaneously equilibrated to a common thermal environment at each stage of the process.

Using a 96-well microplate with a sample in each well as an example, the plate is typically placed in contact with a metal block that is heated and cooled either by a Peltier heating/cooling apparatus or by a closed-loop liquid heating/cooling system that circulates a heat transfer fluid through channels machined into the block. In general, however, rapid changes in temperature that are uniform across all wells or channels are still difficult to achieve.

SUMMARY OF THE INVENTION

To address the need for rapid temperature changes in reaction systems that are retained in the wells of a microplate or in any plate or device that contains an array of individual sample receptacles, the various devices and methods disclosed herein involve the placement of a vapor chamber underneath the plate or device, plus heating elements, cooling elements, or both to allow or induce vaporization and condensation of a working fluid in the vapor chamber. The vapor chamber is arranged such that contact with the heated vapor of the working fluid, and condensation of the vapor when cooled, transfer heat into and draw heat from, respectively, the contents of each sample receptacle by conductive heat transfer between the walls of the vapor chamber and the walls of the receptacles. In certain embodiments of the invention, the top of the vapor chamber is in direct contact with the undersides of the receptacles, while in others an intermediary plate is placed between the undersides of the receptacles and the top of the vapor chamber. In embodiments in which the receptacles are wells and the vapor chamber and the wells are in direct contact, the top surface of the vapor chamber has depressions that are shaped and spaced to receive the wells, and to conform in contour with the undersides of the wells to the extent that the depressions are in direct and continuous contact with the wells. In embodiments in which an intermediary plate is included, the intermediary plate has depressions in its top surface that are shaped and spaced to receive, and that conform in contour to, the sample receptacles, while the bottom surface of the plate is contoured to provide maximal contact with the top surface of the vapor chamber. In many cases where an intermediary plate is used, the bottom surface of the intermediary plate and the top surface of the vapor chamber are both flat for convenience of construction and for low cost. In all embodiments, i.e., both those with the intermediary plate and those without, a single vapor chamber is arranged to control heat transfer into and out of a plurality of sample receptacles, and in many cases all receptacles, such as the wells of a microplate or other multi-well plate or all microchannels of a microfluidics device, serving as a heat spreader and cooling spreader among the various receptacles to achieve uniform and rapid temperature changes among the receptacles. Alternatively, a single vapor chamber can provide heat transfer into and out of a section of a well plate or microfluidics device, the section itself containing a plurality of wells or channels and the vapor chamber thereby spreading the thermal effects among all of the wells or channels with which it is in thermal contact.

Where the walls of the vapor chamber are in direct contact with the walls of the sample receptacles, best results will be achieved when the contours of contacting surfaces are identical in curvature (including no curvature in the case of flat surfaces) but curved in opposite directions. In the case of wells of a multi-well plate, surfaces of the vapor chamber that conform to the undersides of the wells will thereby achieve direct and continuous contact with the undersides of the wells, or at least with portions of the side walls of the wells to heights that will encompass the typical (or expected range of) depths of the reaction mixtures within the wells.

Vaporization and condensation of the working fluid are achieved by heating and cooling of the fluid through the use of heating elements, cooling elements, or both, that are externally controlled, i.e., turned on or off, and in some cases regulated, from outside the vapor chamber. In certain embodiments, a wick structure in the interior of the vapor chamber enhances the movement of the working fluid, particularly during condensation to promote the travel of the condensed fluid away from the reaction wells. In certain constructions, variable and independently controllable thermal coupling means are interposed between the heating element and the vapor chamber, or between the cooling element and the vapor chamber, or both.

These constructions and further variations are described in more detail below.

DETAILED DESCRIPTION OF SELECTED EMBODIMENTS

Figure 1:
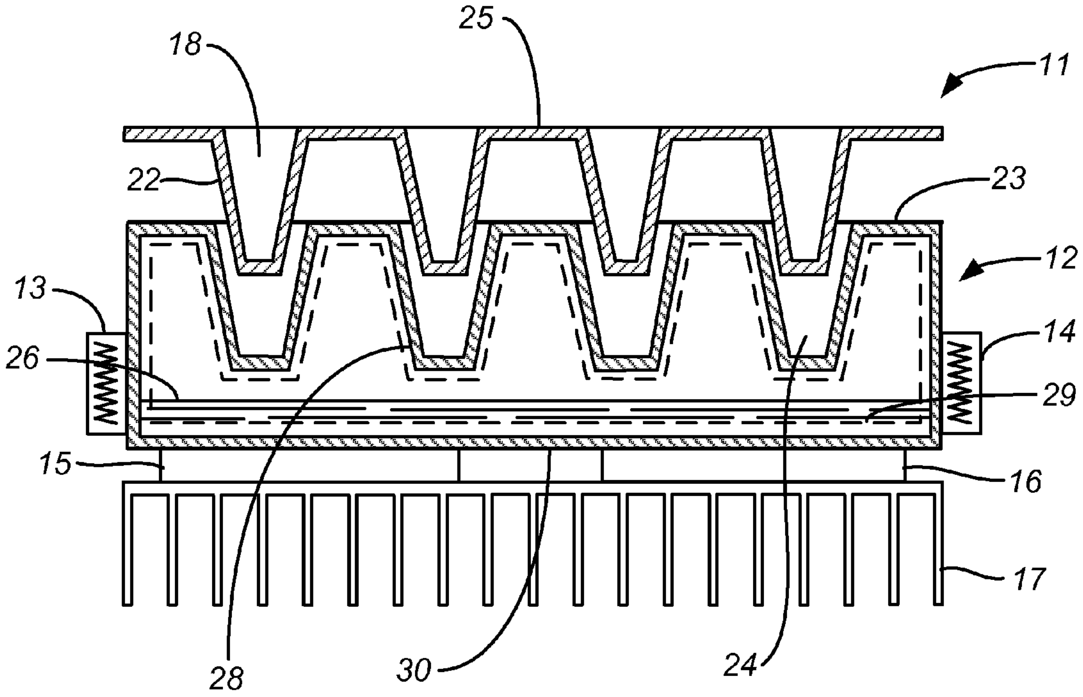
FIG. 1 is a cross section of a combination of a well plate, a vapor chamber, and heating and cooling elements, illustrating certain features of one example of an implementation of the present invention. The well plate in this Figure is raised above the vapor chamber for ease of viewing.

The vapor chamber that forms a component of each of the systems described herein is a hollow body with a closed internal cavity that contains a working fluid whose vaporization and condensation within the cavity serve as means for promoting or accelerating the transfer of heat out of the cavity into the reaction wells or into the cavity from the reaction wells. Thermal contact between the vapor chamber and the sample receptacles occurs in many cases at the top surface of the vapor chamber, either by direct contact with the undersides of the sample receptacles or through the intermediary plate. To accomplish this, the working fluid is generally partially vaporized so that it exists both in liquid and vapor form within the cavity. Heated vapors tend to rise within the cavity, and upon so doing to contact internal surfaces of cavity wall sections that are in direct contact with the walls of the sample receptacles. Condensation of the vapors at those surfaces releases heat from the vapor, and the released heat passes through the walls to heat the reaction mixtures within the receptacles. Conversely, vaporization at the walls draws heat from the receptacles into the cavity with the effect of cooling the reaction mixtures.

In certain embodiments that do not include an intermediary plate, the vapor chamber will have an array of depressions that conform to the sample receptacles, and that therefore extend downward into the internal cavity of the vapor plate. Structural integrity and rigidity of the vapor chamber can be reinforced by using depressions that are deep enough that their lower extremities contact or are fused to the floor of the vapor chamber. In other cases, a gap remains between the lower ends of the depressions and the floor of the chamber to provide additional space for circulation of the working fluid, whether in liquid or vapor form. In embodiments that include an intermediary plate, the vapor chamber can have a top surface that is flat or of any other contour since the vapor chamber does not directly contact the sample receptacles. For most efficient heat transfer, the intermediary plate will have top and bottom surfaces that are complementary in contour to the undersides of the wells and to the vapor chamber, respectively.

For those embodiments in which the sample receptacles are wells of a multi-well plate, the plate will generally be designed as a unitary structure that contains a planar array of wells connected by a deck portion, which is in many cases a flat horizontal portion that forms a continuous surface between all of the wells. In other cases, the deck portion is a network of webs or a flat surface that includes gaps. For manufacturing convenience, many well plates will have a continuous deck portion circling the rims of each of the wells, with no gaps in the deck portion or between the deck and the wells. In many cases, the wells will extend downward from the deck, with convex undersides extending below the deck. The shapes of the wells can vary widely. They can for example be those with hemispherical, elliptical, conical, frustoconical (i.e., truncated conical), cylindrical, or rectangular. For maximal response to temperature changes imposed through the walls of the wells, conical shapes are of particular interest since they offer a high ratio of lateral wall area to internal well volume and thus a large heat transfer area, and each well is readily emptied of liquid reaction media when desired.

Contact between the vapor chamber and the well plate for systems designed for use without an intermediary plate, or between the intermediary plate and the well plate for systems designed for use with an intermediary plate, can include the deck portion of the well plate, although inclusion of the deck portion is unnecessary. In many cases, therefore, only the sides of the reaction wells will be in contact with the vapor chamber or the intermediary plate for thermal transfer, and in many cases, contact need extend only a portion of the distance up the side wall of each reaction well. The reaction wells may thus be deeper than the corresponding depressions in the vapor chamber or the intermediary plate. Well plates with such reaction wells can be used, for example, when the reaction media to be retained within each well occupies only a portion of the well, since heat transfer need only occur as high as the height of the liquid medium in the well. Thus, example, the depths of the depressions can in some cases be one-third to five-sixths the depths of the reaction wells, or one-half to three-quarters the depths, and still provide rapid and effective temperature changes.

The intermediary plates when included will generally be of highly heat-conductive materials so that they will not significantly lower the rates of heat transfer in either direction. In many cases, the intermediary plate will also be of rigid construction to add to the stability and proper alignment of the well plate and the vapor chamber. Metals, for example copper, aluminum, and alloys thereof, are thus particularly useful as materials for intermediary plates.

Certain embodiments of the invention include two or more vapor chambers for further acceleration of heat transfer and to further promote uniformity of temperature among all of the sample receptacles. Two vapor chambers can be included, for example, with an intermediary plate of the type described above in between the two chambers. The lower vapor chamber can provide heat transfer to or from an underlying heating or cooling element.

Controllable heating of the working fluid, as well as controllable cooling, can be achieved by conventional heating and/or cooling elements of the types commonly used in biochemical or chemical laboratory equipment. Resistance heaters and Peltier (thermoelectric) modules are particularly convenient in view of their small size and localized effect. The heating and/or cooling elements can be placed at the sides of the vapor chamber, below the vapor chamber, or generally at any location that will result in rapid or optimal rates of heating and cooling for the particular protocol to be followed. Heat dissipation fins or heat sinks in general to accelerate cooling will also be of use in many cases.

The optimal working fluid is a fluid that provides high heat transfer, is readily volatilized and condensed, and flows readily over the wall surfaces of the vapor chamber. Fluids with high latent heat, high thermal conductivity, low liquid and vapor viscosities, and high surface tension will therefore be useful. Additional characteristics of value in many cases are thermal stability, wettability of wick and wall materials, and a moderate vapor pressure over the contemplated operating temperature range. Fluids that meet these characteristics can be organic or inorganic, the optimal choice depending on the contemplated temperature range. For PCR systems, a working fluid with a useful range of from about 50° C. to about 100° C., i.e., a fluid that is liquid at room (ambient) temperature and liquid at 100° C., at atmospheric pressure, will be most appropriate. Examples are acetone, methanol, ethanol, water, toluene, and any of these liquids with surfactants dissolved therein.

The partially vaporized working fluid can occupy the vapor chamber cavity on its own, or be mixed with a diluent gas that remains gaseous throughout the temperature cycling. Most efficient heat transfer however will often be achieved with an undiluted working fluid. Since the vapor chamber is a closed chamber, the heating and cooling of the working fluid will be accompanied by pressure changes. In many cases, particularly when the working fluid is undiluted it or essentially undiluted (i.e., diluted only with proportions of diluent gas that are small enough not to affect the diffusion rate of gaseous working fluid molecules throughout the cavity), it will be advantageous to select a working pressure range that will provide vaporization and condensation at temperatures that will match those of the temperature cycle that is sought for the samples in the reaction wells. The cavity can first be evacuated or partially evacuated, and the working fluid added in vapor form or in liquid form to vaporize upon entering the evacuated cavity, and resulting pressure will vary with the amount of working fluid thus introduced. Evacuation to less than 200 mm Hg, and in many cases less than 100 mm Hg or even less than 25 mm Hg, will be useful in many cases. The operating pressure range during the thermal cycling can then range from subatmospheric to atmospheric or superatmostpheric, although in many cases the pressure range over the full cycle will remain subatmospheric, such as for example between 200 mm Hg and 500 mm Hg. All pressures cited in this paragraph are absolute pressures.

As noted above, certain embodiments of the invention include a wicking means or wick structure in the vapor chamber. The wick structure can be a lining on a portion or all of the wall surface of the internal cavity of the vapor chamber, and aids in the flow of the working fluid over the internal surfaces of the vapor chamber to distribute the cooling and heating effects throughout the chamber cavity and thus increase the response to temperature changes and the uniformity of the temperature through the chamber and hence the sample receptacles. The wick structure thus promotes the flow of the condensate within the vapor chamber. Examples of wick structures are porous materials, typically made of metal foams, felts, or meshes of various pore sizes, in all cases lining the interior walls of the vapor chamber. Further examples are fibrous materials, notably ceramic fibers or carbon fibers. Wick structures can also be capillaries in the form of axial grooves in the vapor chamber wall, or a layer of dendritic metallic crystals such as copper dendrites.

The drawings provided herewith and the accompanying descriptions below are directed to systems where the sample receptacles are wells of a multi-well plate. Constructions in which the sample receptacles are channels of a microfluidics device are analogous.

The apparatus shown in FIG. 1 includes a well plate 11 poised above a vapor chamber 12, together with a pair of resistance heaters 13, 14 serving as heating elements, a pair of thermoelectric modules 15, 16 serving as cooling elements, and a finned heat sink 17 to disperse the heat drawn from the vapor chamber 12 by the thermoelectric modules 15, 16. While only four wells 18 of the well plate are shown, the well plate 11 will commonly be any plate with a two-dimensional array of wells, such as a microplate with 96 wells in an 8×12 rectangular array, although plates with larger or smaller numbers of wells are often used. The well plate is typically made of a thin material and is highly thermally conductive, and is often a consumable component, i.e., one that is discarded after a single use. The plate is made from a single sheet that is planar except for the wells 18 which extend downward, the undersurfaces 22 of the wells being generally convex. In the example shown, the undersurfaces are truncated cones. The vapor chamber 12, which underlies the entire well plate 11, has an upper surface 23 that contains depressions 24 in the same spatial arrangement as the wells 18 of the well plate and complementary to the wells in shape. The depressions 24 form truncated cones identical to the truncated cones of the undersurfaces 22 of the wells except that the depressions are concave rather than convex. Thus, when the well plate 11 is fully lowered onto the vapor chamber 12, there is full surface contact between each well and the vapor chamber. In the construction shown, surface contact is achieved not only at the wells 18, but also at the flat sections 25, i.e., the deck portion, of the plate between the wells. An equally effective construction, as noted above, is one in which continuous surface contact is present only at the wells and not at the deck portion.

The vapor chamber 12 is a fully enclosed chamber with a hollow interior. A working fluid, when in liquid form, forms a shallow layer on the floor of the chamber whose liquid level 26 is below the lower ends of the depressions 24. When vaporized, the working fluid forms a vapor that rises to the upper regions of the chamber to contact the undersides 28 of the depressions 24. A wick structure 29 lines the interior wall surface of the chamber.

While the apparatus shown in FIG. 1 includes two resistance heating elements 13, 14, one on each of opposing lateral sides of the vapor chamber 12, the number and placement of the heating elements is not critical and can vary considerably. Distribution of the heat generated by the heating element(s) is achieved by the wick structure 29, which can be selected and arranged within the vapor chamber to provide the maximum effectiveness for any choice and arrangement of heating element(s). The two thermoelectric modules 15, 16 are arranged side-by-side underneath, and contacting, the bottom surface 30 of the vapor chamber. As with the heating elements 13, 14, the number and placement of the thermoelectric modules can vary considerably while the wick structure can be selected and arranged to provide the modules with their maximum cooling effect. For example, the heating elements can be placed in contact with the bottom surface of the vapor chamber while the cooling elements are placed in contact with the sides, or both can be placed on the sides, or both on the bottom. The heating elements can be those employing resistance heating as shown, or any other conventional heating units that are externally controlled and responsive to commands such as electrical signals, such as thermoelectric modules wired to heat rather than cool. Likewise, the thermoelectric modules can be replaced by any other conventional cooling units that are externally controlled and responsive to commands.

Changes in heating and cooling can be made more rapid by the interposition of controllable thermal couplings between the heating/cooling elements and the exterior surface of the vapor chamber. By "thermal coupling" is meant a substance or component that allows the passage of heat energy between the heating/cooling element(s) and the vapor chamber wall, and by "controllable thermal coupling" is meant a thermal coupling that can be switched at will from a high rate of heat flow to a low rate, and vice versa. Thus, when the apparatus is in a heating phase of a temperature cycle, a controllable thermal coupling at a heating element can be activated to a condition producing a high rate of heat transfer while the controllable thermal coupling at a cooling element is switched to a position in which the heat transfer rate is relatively low.

Figure 2:
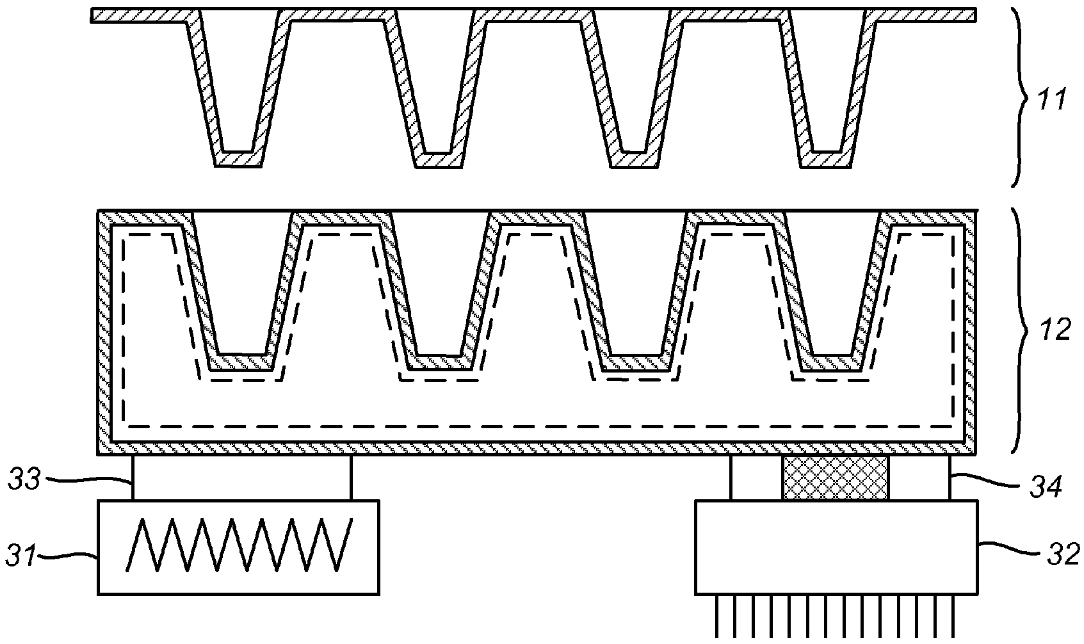
FIG. 2 is a cross section of the well plate of FIG. 1 in combination with a different arrangement of vapor chamber and heating and cooling elements, as well as thermal coupling components, again illustrating features of certain embodiments of the present invention.

One means by which a controllable thermal coupling can be achieved is shown in FIG. 2, which depicts the placement of a ferrofluid or a ferrofluidic seal between the heating/cooling element and the vapor chamber wall. In the structure shown, the heating element 31 and the cooling element 32 are both positioned on the underside of the vapor chamber 12, and separate ferrofluidic seals 33, 34 reside between the heating and cooling elements respectively and the vapor chamber. Imposition of a magnetic field will cause thermally conductive particles in the fluid to become magnetized and to either align or cluster. Depending on the orientation of the field, the particles when magnetized can form a bridge between the heating/cooling element and the vapor chamber wall and, when demagnetized, disrupt such a bridge that is otherwise formed. In the condition shown in the Figure, the ferrofluidic seal 33 at the heating element is not energized and does not form a thermal bridge between the element and the vapor chamber, while the ferrofluidic seal 34 at the cooling element is energized and forms a thermal bridge with the vapor chamber to enhance the cooling effect. In an alternative structure (not shown), a cooling element covers the entire underside of the vapor chamber while the heating element is at the side of the vapor chamber or at the top (laterally spaced from the wells), and a single layer of ferrofluid resides beneath the vapor chamber between the vapor chamber and the cooling element. As alternatives to ferrofluidic seals, mechanical means can be used to establish contact between the heating and cooling elements and the vapor chamber for good thermal coupling. Such mechanical means might include a movable support that can be raised to make contact and lowered to break contact. Further alternatives are the use of thermally conductive grease or a thermally conductive liquid or metal between the heating and cooling elements and the vapor chamber.

Figure 3:
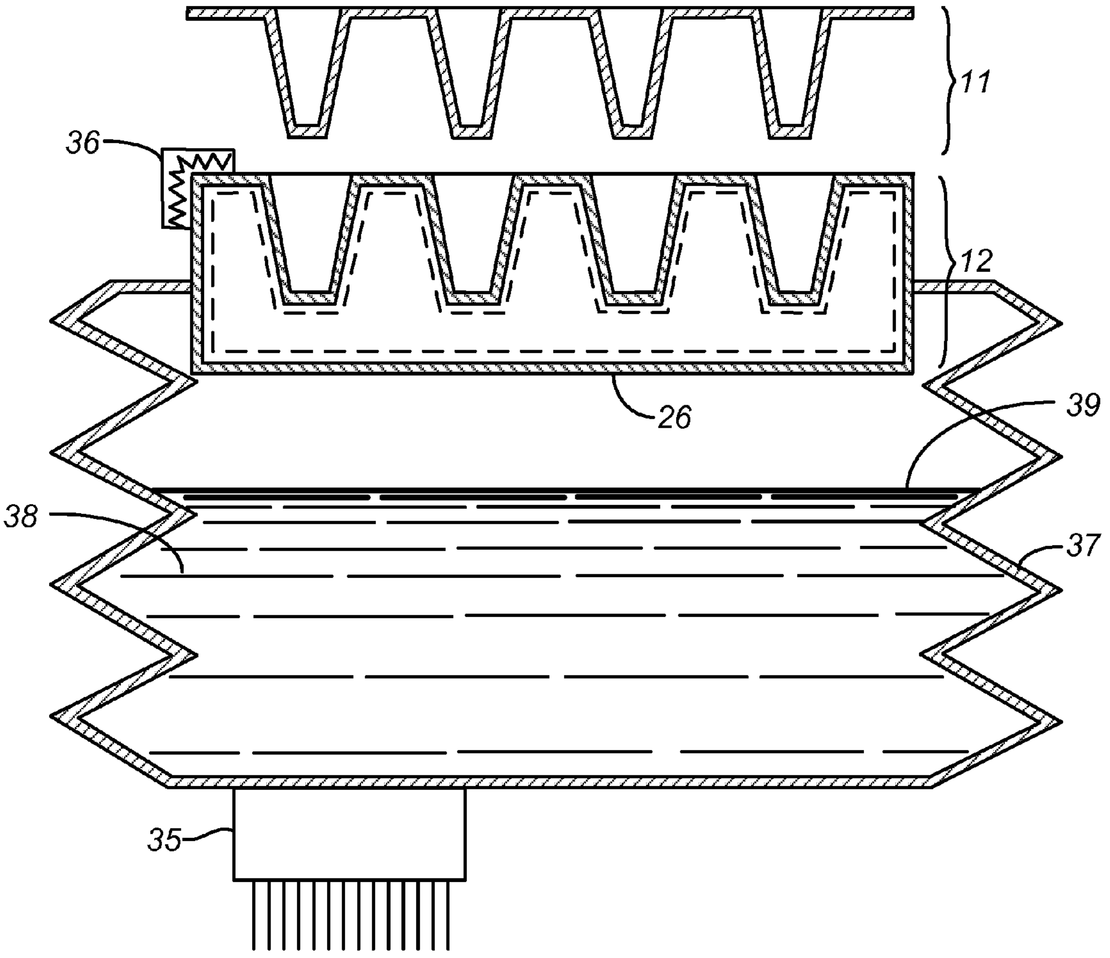
FIG. 3 is a cross section of the well plate of FIG. 1 in combination with a still different arrangement of vapor chamber, heating and cooling elements, and with controllable thermal coupling, as a further illustration of features of certain embodiments of the present invention.

Another means of thermal coupling is shown in FIG. 3, in which a liquid layer of variable height serves as the thermal coupling between the cooling element 35 and the vapor chamber 12. In this example, the heating element 36 is positioned on an upper corner of the vapor chamber 12, and the cooling element 35 is joined to the bottom of an accordion-shaped liquid bladder 37 positioned on the underside of the vapor chamber 12. When the bladder 37 is extended as shown, the liquid 38 only partially fills the bladder interior, leaving a gap between the liquid level 39 and the underside 26 of the vapor chamber. When the bladder is compressed upward to close the gap and cause the liquid level 39 to contact the underside 26 of the vapor chamber, the thermal bridge is formed. Vent holes (not shown) can be included to allow air to escape from the bladder.

Figure 4:
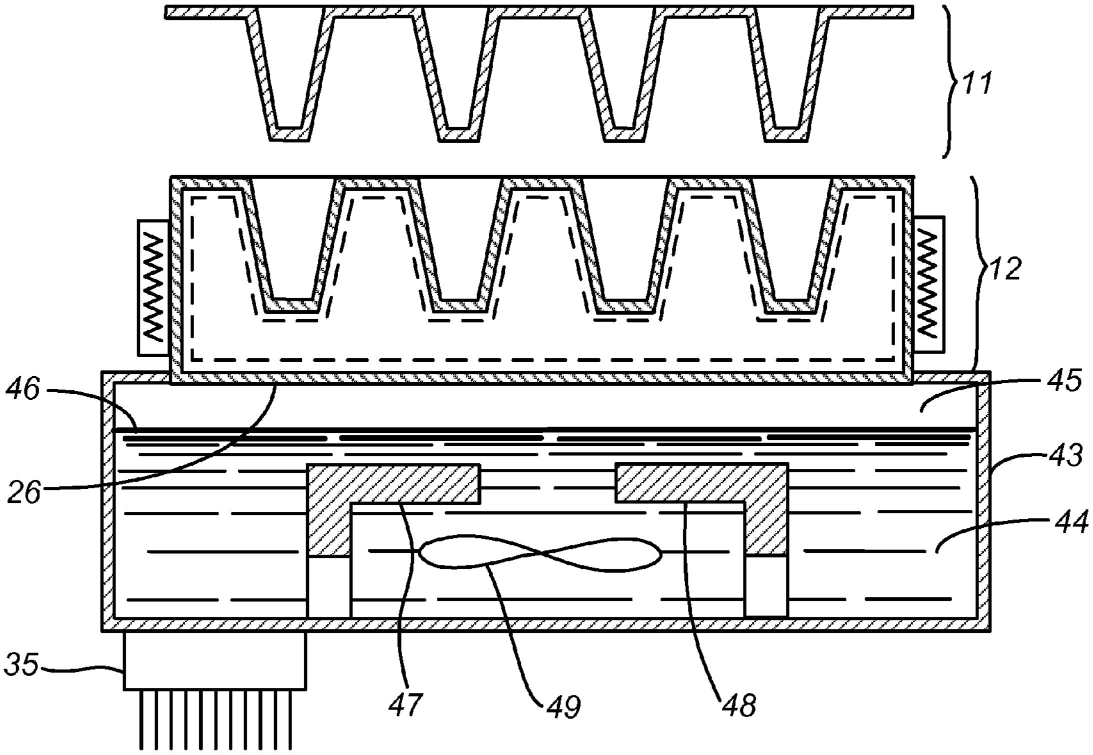
FIG. 4 is a cross section of the well plate of FIG. 1 in combination with a fourth different arrangement of vapor chamber, heating and cooling elements, and thermal coupling, as a still further illustration of features of certain embodiments of the present invention.

A still further means is shown in FIG. 4, in which a liquid spray is used to enhance the thermal contact between the cooling element 35 and the vapor chamber 12. Two heating elements 41, 42 are used in this example, one on each of two opposing lateral sides of the vapor chamber 12, and the cooling element 35 is joined to the vapor chamber 12 through an intervening chamber 43 that is partially filled with a heat transfer liquid 44 with either a vacuum or an air gap 45 between the liquid layer 46 and the underside 26 of the vapor chamber. During a heating cycle, the vacuum or air gap 45 serves as a thermal barrier, and during a cooling cycle, electrical nozzles 47, 48 are energized to spray the heat transfer liquid upwards against the vapor chamber underside. The nozzles can be of the type used in an inkjet printer, or can be fed by a pump. A magnetic stirrer 49 causes circulation of the liquid to increase the cooling effect. The magnetic stirrer can also be used as an impeller pump to drive liquid outwards and up to make contact with the underside of the vapor chamber, without the use of nozzles.

Figure 5:
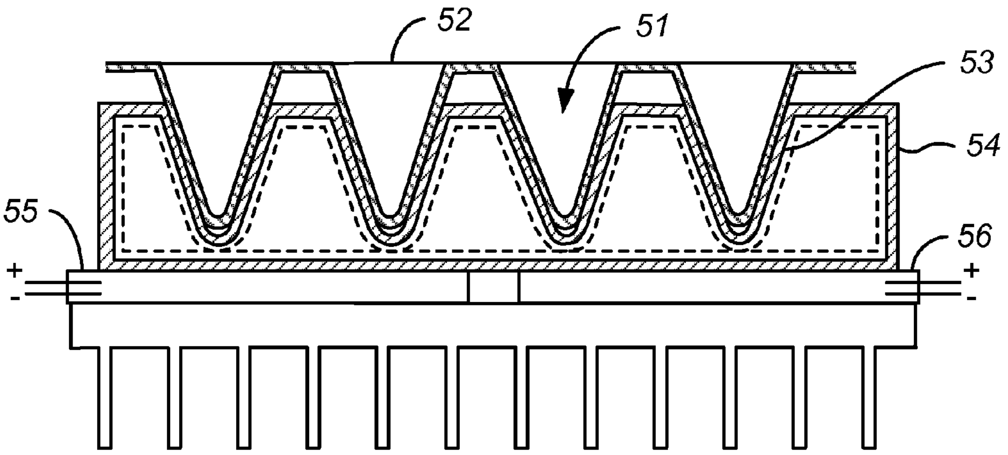
FIG. 5 is a cross section of a further embodiment of the present invention, with the vapor chamber in direct contact with the well plate as in the preceding figures.

In the embodiment of FIG. 5, the wells 51 of the well plate 52 are deeper than the depressions 53 in the top surface of the vapor chamber 54. The only portion of each well that directly receives the full benefit of the vaporizations and condensations in the vapor chamber 54 is therefore approximately the lower two-thirds of each well, which is the portion that will contain the reaction mixture. Heating and cooling in this embodiment are both achieved by thermoelectric modules 55, 56 in contact with the undersides of the vapor chamber.

Figure 6:
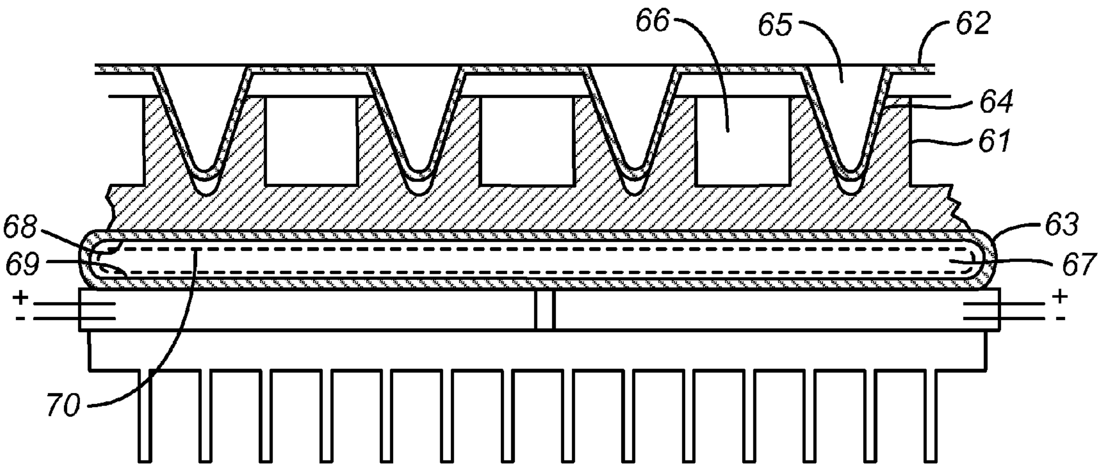
FIG. 6 is a cross section of a still further embodiment of the present invention, with an intermediary plate interposed between the vapor chamber and the well plate.

FIG. 6 depicts a still further embodiment, containing an intermediary heat transfer plate 61 interposed between the sample plate 62 and the vapor chamber 63. Depressions 64 in the intermediary plate match the spacing and contours of the undersides of the reaction wells 65 in the same manner as to the depressions 53 of the embodiment of FIG. 5. In between the depressions 64 are hollows 66 to reduce the mass of the intermediary plate. The vapor chamber 63 in this embodiment is generally flat, with an internal cavity 67 that has a flat internal upper surface (ceiling) 68 and a flat internal lower surface (floor) 69, and a wicking structure 70 lining both surfaces. The planar top surface of the vapor chamber provides continuous contact with the planar lower surface of the intermediary plate.

Figure 7:
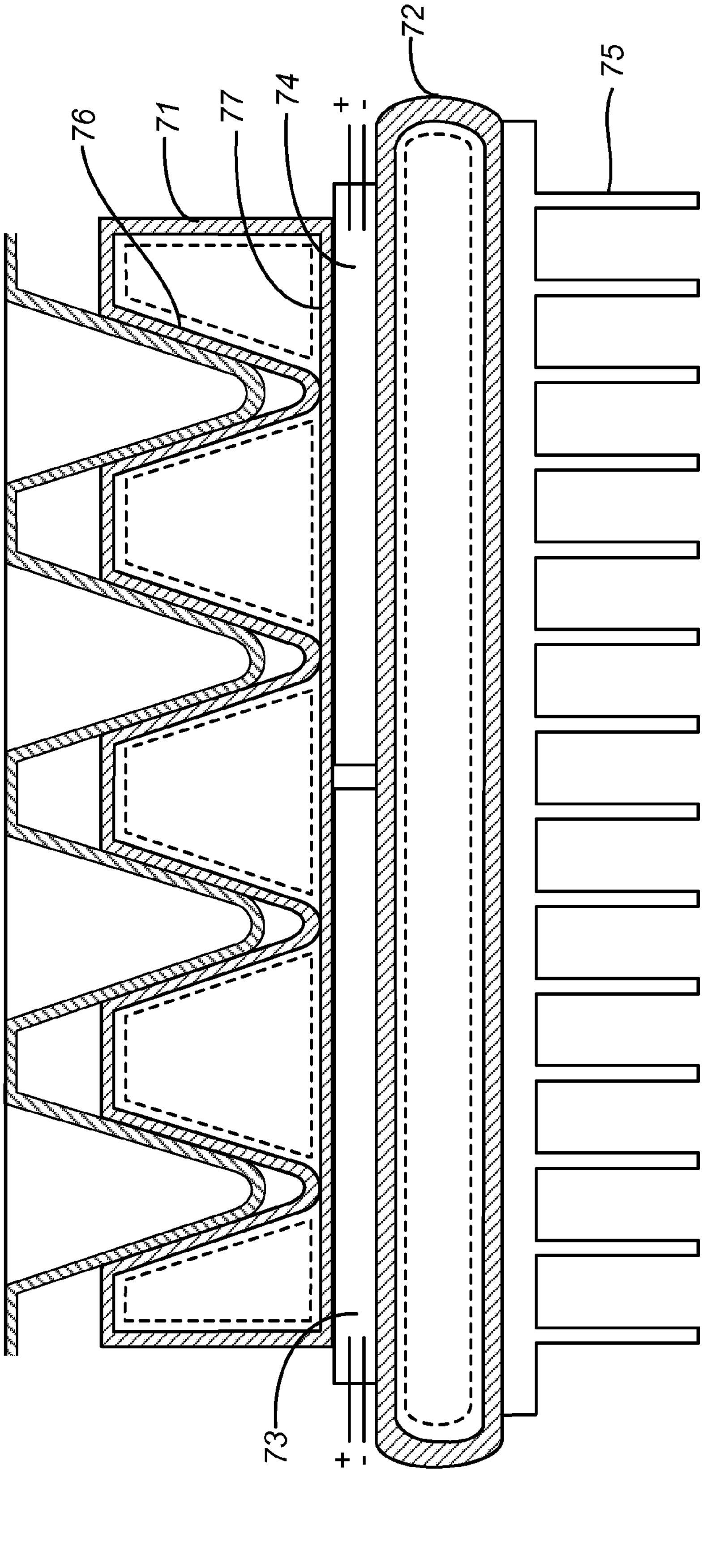
FIG. 7 is a cross section of a still further embodiment of the present invention, incorporating two vapor chambers.

FIG. 7 represents a still further variation, this time with two vapor chambers 71, 72. The upper vapor chamber 71 serves the same function as the vapor chamber 54 of FIG. 5, while the lower vapor chamber 72, which is similar in shape to the vapor chamber 63 of FIG. 6, is interposed between the two thermoelectric modules 73, 74 and the heat sink 75. The lower vapor chamber 72 thus improves the functionality of the modules by accelerating the rate of heat transfer between each module and the underlying heat sink. In this embodiment as well, the depressions 76 in the upper vapor chamber 71 reach the floor 77 of the vapor chamber cavity.

The structures shown in these Figures are merely illustrative; other examples and variations on the examples shown that utilize the central principles of a vapor chamber according to this invention will be readily apparent to those of skill in the art.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An apparatus for thermal cycling in an array of sample receptacles, said apparatus comprising:

a hollow body having a single internal cavity with a working fluid therein that is partially vaporized, wherein said hollow body has a top surface with depressions therein that are spaced and shaped to receive a plurality of sample receptacles and thereby to place said depressions in direct and continuous contact with said undersides of said sample receptacles, said hollow body arranged to cause conductive heat transfer between walls of said cavity and walls of all of said sample receptacles, and wherein said internal cavity of said hollow body has a substantially flat floor and said depressions have undersides internal to said cavity that contact said flat floor; and one or more element that controllably heats said working fluid, cools said working fluid, or both, within said cavity to cause vaporization and condensation of said working fluid, wherein said element is below or at a side of the hollow body.

2. The apparatus of claim 1 wherein said sample receptacles are wells of a multi-well plate, which further comprises a deck portion joining said wells, said wells having undersides that extend downward from said deck portion, said hollow body arranged to cause conductive heat transfer between walls of said cavity and said undersides of said wells.

3. The apparatus of claim 2 further comprising a thermally conductive intermediary plate interposed between said multiwell plate and said hollow body, said intermediary plate having a top surface with depressions therein that are spaced and shaped to receive said wells and upon doing so to be in direct and continuous contact with said undersides of said wells, said intermediary plate being in conductive heat transfer contact with said hollow body.

4. The apparatus of claim 2 wherein said undersides of said reaction wells are either conical or frustoconical in shape.

5. The apparatus of claim 1 wherein said sample receptacles are channels of a microfluidics device.

6. The apparatus of claim 1 further comprising a wick structure within said cavity to promote distribution of condensed working fluid over surfaces of said cavity.

7. The apparatus of claim 1 wherein said element that controllably heats said working fluid comprises a resistance heater.

8. The apparatus of claim 1 wherein said one or more element that controllably heats said working fluid, cooling said working fluid, or both, comprise a thermoelectric module.

9. The apparatus of claim 8 wherein said thermoelectric module is thermally coupled to said hollow body by a controllable thermal coupling.

10. The apparatus of claim 9 wherein said controllable thermal coupling is a ferrofluid.

11. The apparatus of claim 9 wherein said controllable thermal coupling comprises a body of heat transfer liquid interposed between said element and said hollow body and a mechanism for raising and lowering said body of heat transfer liquid.

12. The apparatus of claim 9 wherein said controllable thermal coupling comprises a body of heat transfer liquid interposed between said element and said hollow body and a nozzle for spraying said heat transfer liquid against said hollow body.

13. The apparatus of claim 1 wherein the apparatus comprises (i) the element that controllably heats said working fluid comprises a resistance heater and (i) the element that controllably cools said working fluid comprises a thermoelectric module.

14. The apparatus of claim 1, wherein said element is below the hollow body.

15. A method for thermally cycling a plurality of reaction mixtures through a preselected sequence of temperatures using the apparatus of claim 1, said method comprising:

(a) placing said reaction mixtures in individual sample receptacles comprising reaction wells of a multi-well sample plate;

(b) placing said sample plate in thermal contact with the hollow body of the apparatus, to promote conductive heat transfer between walls of said cavity and walls of all of said sample receptacles; and (c) heating and cooling said working fluid to evaporate and condense, respectively, said working fluid according to a timing sequence and temperature protocol selected to achieve said preselected sequence of temperatures in said reaction mixtures.

16. The method of claim 15 wherein said sample plate comprises a deck portion joining said sample receptacles, said reaction wells having undersides that extend downward from said deck portion, and step (b) comprises placing said multi-well plate in contact with said hollow body to achieve said direct and continuous contact.

17. The method of claim 15 wherein step (c) comprises cooling said working fluid with a thermoelectric module contacting said hollow body through a controllable thermal coupling.

18. The method of claim 15 wherein said hollow body has a floor, said method further comprising drawing condensed working fluid toward said floor by wicking means during cooling of said working fluid.

19. The method of claim 15 further comprising interposing a thermally conductive intermediary plate between said sample plate and said hollow body, said intermediary plate providing direct and continuous contact with both said undersides of said sample receptacles and said hollow body.

* * * * *